United States Patent [19]

Ingendoh et al.

[11] Patent Number: 4,588,723

[45] Date of Patent: May 13, 1986

[54] AMINOALKYL-IMIDAZOTHIADIAZOLE-ALKENECARBOXYLIC ACID AMIDES, INTERMEDIATES FOR THEIR PREPARATION AND THEIR USE IN MEDICAMENTS

[75] Inventors: Axel Ingendoh, Velbert; Horst Meyer, Wuppertal; Bernward Garthoff, Hilden, all of Fed. Rep. of Germany

[73] Assignee: Bayer Aktiengesellschaft, Leverkusen, Fed. Rep. of Germany

[21] Appl. No.: 634,851

[22] Filed: Jul. 26, 1984

[30] Foreign Application Priority Data

Aug. 17, 1983 [DE] Fed. Rep. of Germany ....... 3329621

[51] Int. Cl.[4] .................. A61K 31/425; C07D 513/04
[52] U.S. Cl. ..................... 514/231; 514/255; 514/256; 514/307; 514/314; 514/322; 514/338; 514/363; 514/80; 514/121; 514/128; 514/130; 514/131; 514/134; 514/333; 514/405; 546/144; 546/167; 546/187; 546/193; 546/199; 546/271; 546/335; 548/126

[58] Field of Search ............... 548/126; 544/80, 121, 544/128, 130, 131, 134, 333, 405; 546/144, 167, 187, 193, 199, 271, 335, 359; 424/248.51, 250, 251, 258, 263, 267, 270; 514/231, 255, 256, 307, 314, 322, 338, 363

[56] References Cited

U.S. PATENT DOCUMENTS 4,444,770 4/1984 Meyer et al. .................. 548/126 X Primary Examiner—Richard L. Raymond
Attorney, Agent, or Firm—Sprung Horn Kramer & Woods

[57] ABSTRACT

The invention relates to aminoalkyl-imidazothiadiazole-alkenecarboxylic acid amides, processes for their preparation, intermediates which are used in their preparation, medicaments containing said active compounds for use as antihypertensive agents, diuretics and uricosuric agents. Also included in the invention are methods for use of said compounds and compositions for the above indicated indications. The active compounds are identified herein by formula (I) and the novel intermediates used in preparing the compounds of Formula (I) are those described herein under Formula (II).

20 Claims, No Drawings

AMINOALKYL-IMIDAZOTHIADIAZOLE-ALKENECARBOXYLIC ACID AMIDES, INTERMEDIATES FOR THEIR PREPARATION AND THEIR USE IN MEDICAMENTS

The present invention relates to aminoalkylimidazothiadiazole-alkenecarboxylic acid amides, various processes for their preparation, intermediates which are used in their preparation, and medicaments containing the new compounds, in particular antihypertensive agents, diuretics and uricosuric agents. The invention relates to aminoalkyl-imidazothiadiazole-alkenecarboxylic acid amides of the formula (I)

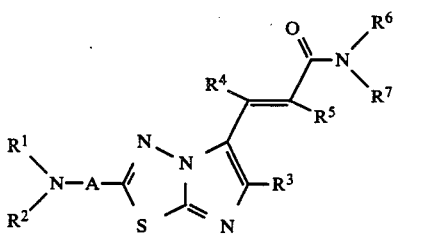

in which
- $R^1$ denotes hydrogen, aryl or an aliphatic hydrocarbon radical which is optionally interrupted by O, S, N, N-alkyl, NH, N-aryl or N-aralkyl and is optionally substituted by hydroxyl, alkoxy, alkyl, trifluoromethyl, halogen, phenyl, alkoxycarbonyl or dialkylamino, it being possible for the two alkyl radicals optionally to form, together with the N atom, a 5-membered to 7-membered ring, which is optionally interrupted by a hetero-atom from the group comprising O, S, NH and N-alkyl, and these abovementioned alkyl and phenyl radicals in turn optionally being substituted by halogen, trifluoromethyl, alkyl, aryl, aralkyl, alkoxy, alkylmercapto or $SO_2$-alkyl,
- $R^2$ has the meaning given for $R^1$, it being possible for $R^2$ and $R^1$ to be identical or different, or $R^2$ together with $R^1$ forms, with the nitrogen atom, a 3-membered to 8-membered saturated or unsaturated ring which optionally contains 1 or 2 other hetero-atoms from the group comprising oxygen, sulphur and nitrogen, the nitrogen optionally being substituted by hydrogen, alkyl, aryl or aralkyl, and it being possible for this 3-membered to 8-membered ring to be substituted by 1 to 4 identical or different substituents from the group comprising alkyl, halogen, aryl, aralkyl, alkoxycarbonyl, hydroxyalkyl, alkoxyalkyl and trifluoromethyl, or it being possible for this ring to be fused with an aromatic ring,
- A represents a chain (preferably an alkylene chain) of 1–4 carbon atoms which is optionally interrupted by 1 or 2 hetero-atoms from the group comprising oxygen, sulphur and nitrogen and can be saturated or unsaturated or part of a 3-membered to 8-membered ring, and in which each nitrogen and carbon atom can be substituted by radicals $R^1$, which can be identical or different,
- $R^3$ has the meaning given for $R^1$ and is identical to or different from $R^1$, or represents furyl, phenyl, thienyl, pyrimidyl, pyrazinyl, quinolinyl, isoquinolinyl or pyridyl, the rings optionally being substituted by 1, 2 or 3 identical or different substituents from the group comprising alkyl, aryl, alkoxy, halogen, nitro, trifluoromethyl, $SO_n$-alkyl (n=0, 1 or 2) or $NR^9R^{10}$, wherein
- $R^9$ and $R^{10}$ have the abovementioned meaning of $R^1$ and $R^2$,
- $R^4$ represents hydrogen, trifluoromethyl or alkyl,
- $R^5$ represents hydrogen, alkyl, cyano, halogen, nitro, $SO_n$-alkyl (n=0, 1 or 2) or $CXR^8$, wherein
- X denotes O or S and
- $R^8$ has the abovementioned meaning of $R^1$, and $R^6$ and $R^7$ each have the meaning given for $R^1$ and are identical to or different from $R^1$, or, together with the nitrogen atom, form a 3-membered to 8-membered saturated or unsaturated ring which optionally contains one or two further heteroatoms from the group comprising oxygen, sulphur and nitrogen, the nitrogen optionally being substituted by hydrogen, alkyl, aryl or aralkyl, and this 3-membered to 8-membered ring optionally being substituted by 1, 2, 3 or 4, preferably 1 or 2, identical or different substituents from the group comprising alkyl, aryl, aralkyl, halogen, hydroxyl, alkoxycarbonyl, hydroxyalkyl, alkoxyalkyl, alkoxy and trifluoromethyl, and it being possible for this ring to be fused with an aromatic ring which is optionally substituted by one to three of these substituents, and their stereoisomeric forms of the various enantiomers, diastereomers and E/Z isomers, and their pharmaceutically acceptable acid addition salts.

In the above substituent definitions, the expression "aryl" represents an aromatic (preferably mono- or bicyclic carbocyclic) hydrocarbon radical with 6 to 14 C atoms, preferably 6 to 10 C atoms, in particular phenyl or naphthyl.

The expression "aliphatic hydrocarbon radical" represents a straight-chain, branched, cyclic, saturated or unsaturated (preferably mono-unsaturated) hydrocarbon radical with 1 to 12 C atoms, in particular with 1 to 6 C atoms.

The expression "alkyl" represents a saturated, straight-chain, branched or cyclic alkyl radical with 1 to 10 C atoms, in particular with 1 to 6 C atoms.

The expression "aralkyl" represents an alkylene group with 1 to 6 C atoms, preferably 1 to 4 C atoms, particularly one or two C atoms which is substituted by aryl (as defined above), preferably phenyl or naphthyl.

The expression "alkoxy" represents an alkoxy radical with 1 to 12 C atoms, in particular with 1 to 6 C atoms, which can be straight-chain or branched. "Halogen" preferably represents fluorine, chlorine or bromine.

The present invention preferably relates to compounds of the formula (I) in which
- $R^1$ denotes hydrogen, aryl or an aliphatic hydrocarbon radical which is optionally interrupted by O, S, N, N-alkyl or NH and is optionally substituted by hydroxyl, alkoxy, alkyl, trifluoromethyl, halogen, alkoxycarbonyl or dialkylamino, the two alkyl radicals optionally forming, together with the N atom, a 5-membered to 7-membered ring which is optionally interrupted by a heteroatom from the group comprising O, S, NH and N-alkyl, and these abovementioned alkyl and phenyl radicals in turn optionally being substituted by halogen, trifluoromethyl, alkyl, alkoxy, alkylmercapto or $SO_2$-alkyl,
- $R^2$ has the meaning given for $R^1$, it being possible for $R^2$ and $R^1$ to be identical or different, or $R^2$ together with $R^1$ forms, with the nitrogen atom, a 5-membered to 7-membered saturated or unsaturated ring which optionally contains 1 or 2 further hetero-atoms from the group comprising oxygen, sulphur and nitrogen, the nitrogen optionally being substituted by hydrogen or alkyl, and it being possible for this 5-membered to 7-membered ring to be substituted by 1 to 4 identical or different substituents from the group comprising alkyl, halogen, aryl, aralkyl, alkoxycarbonyl, hydroxyalkyl, alkoxyalkyl and trifluoromethyl, A represents a chain of 1–4 carbon atoms which is optionally interrupt a hetero-atom from the group comprising oxygen, sulphur and nitrogen and can be saturated or unsaturated or part of a 4-membered to 7-membered ring, and in which each nitrogen and carbon atom can be substituted by radicals $R^1$, which can be identical or different, $R^3$ represents a phenyl, naphthyl, furyl, thienyl, pyrimidyl, pyrazinyl, quinolyl, isoquinolyl or pyridyl radical which is optionally substituted by 1 to 3 identical or different substituents from the group comprising halogen, nitro, trifluoromethyl, alkyl, alkoxy, dialkylamino and $SO_n$-alkyl ($n=0$, 1 or 2), the alkyl and alkoxy radicals mentioned in each case containing 1–4 carbon atoms, $R^4$ represents hydrogen, trifluoromethyl or alkyl, $R^5$ represents hydrogen, alkyl, cyano, halogen or $CXR^8$, wherein X denotes O or S and $R^8$ has the abovementioned meaning of $R^1$, and $R^6$ and $R^7$ each have the meaning given for $R^1$ and are identical to or different from $R^1$, or together with the nitrogen atom form a 5-membered to 7-membered saturated or unsaturated ring which optionally contains 1 or 2 further hetero-atoms from the group comprising oxygen, sulphur and nitrogen, the nitrogen optionally being substituted by hydrogen, alkyl with 1 to 4 carbon atoms, phenyl or benzyl, and their stereoisomeric forms and their pharmaceutically acceptable acid addition salts.

Compounds which may be particularly singled out are those of the formula (I) in which $R^1$ denotes hydrogen or a straight-chain, branched or cyclic, saturated aliphatic hydrocarbon radical which is optionally interrupted by O, S, N, N-alkyl or NH and is optionally substituted by hydroxyl, alkoxy, alkyl, trifluoromethyl, halogen, alkoxycarbonyl or dialkylamino, $R^2$ has the meaning given for $R^1$, it being possible for $R^2$ and $R^1$ to be identical or different, or $R^2$ together with $R^1$ forms, with the nitrogen atom, a 5-membered to 7-membered saturated or unsaturated ring which optionally contains 1 or 2 further hetero-atoms from the group comprising oxygen, sulphur and nitrogen, the nitrogen optionally being substituted by hydrogen or alkyl, and it being possible for this 5-membered to 7-membered ring to be substituted by 1 to 4 identical or different substituents from the group comprising alkyl, halogen, aryl, aralkyl, alkoxycarbonyl, hydroxyalkyl, alkoxyalkyl and trifluoromethyl, A represents a chain (preferably an alkylene chain) of 1–4 carbon atoms which is optionally interrupted by oxygen or nitrogen and can be saturated or unsaturated or part of a 4-membered to 7-membered ring, and in which each nitrogen or carbon atom can be substituted by radicals $R^1$, which can be identical or different, $R^3$ represents a phenyl, furyl, naphthyl, thienyl, pyrimidyl, pyrazinyl, quinolyl, isoquinolyl or pyridyl radical which is optionally substituted by one or two identical or different substituents from the group comprising halogen, nitro, trifluoromethyl, alkyl, alkoxy, dialkylamino and S-alkyl, the alkyl and alkoxy radicals mentioned in each case containing 1 to 4 carbon atoms, $R^4$ and $R^5$ are identical or different and represent hydrogen or alkyl with 1 to 4 carbon atoms and $R^6$ and $R^7$ have the meaning given for $R^1$ and are identical to or different from $R^1$, or together with the nitrogen atom form a 5-membered to 7-membered ring which is optionally interrupted by an oxygen or nitrogen atom, the nitrogen optionally being substituted by hydrogen, alkyl with 1–4 carbon atoms or benzyl, and their stereoisomeric forms of the various enantiomers, diastereomers and Z/E isomers and their pharmaceutically acceptable acid addition salts.

The imidazothiadiazole-alkenecarboxylic acid amides of the formula (I) according to the invention are prepared by a process in which (a) a carbonyl compound of the formula (II)

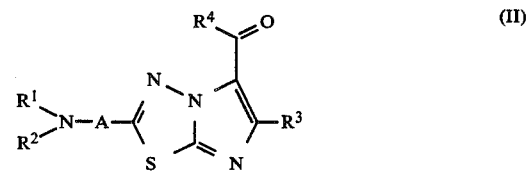

in which A and $R^1$ to $R^4$ have the abovementioned meaning, is reacted with a phosphonate compound of the formula (III)

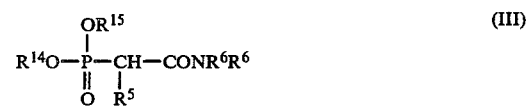

in which $R^5$ to $R^7$ have the abovementioned meaning and $R^{14}$ and $R^{15}$ represent optionally substituted alkyl or aralkyl, in the presence of a strong base and in inert organic solvent at a temperature between $-20°$ and $110°$ C., or (b) acarbonyl compound of the formula (II) is reacted with an acetamide derivative of the formula (V)

in which $R^5$, $R^6$ and $R^7$ have the abovementioned meaning, in the presence of an acid or basic catalyst and if appropriate in the presence of an inert organic solvent at a temperature between $20°$ and $200°$ C., or (c) an alkenecarboxylic acid of the formula (VI)

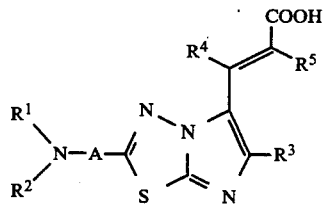

(VI)

in which $R^1$ to $R^5$ have the abovementioned meaning, is amidated with an amine of the formula (VII)

$$HNR^6R^7 \quad (VII)$$

in which $R^6$ and $R^7$ have the abovementioned meaning, if appropriate after activation of the carboxyl group via the corresponding acid chloride (for example by thionyl chloride), in the customary manner in an organic inert solvent at a temperature between 20° and 150° C., or (d) an imidazothiadiazole -alkenecarboxylic acid amide of the formula (VIII)

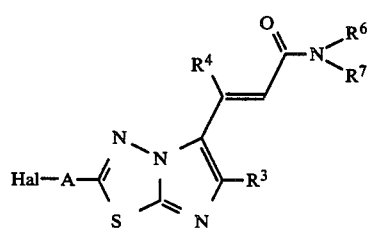

(VIII)

in which

A and $R^3$ to $R^7$ have the abovementioned meaning and

Hal represents an element from the series comprising chlorine, bromine and iodine, is reacted with an amine of the formula $R^1R^2NH$, in which $R^1$ and $R^2$ have the abovementioned meaning, in a suitable solvent at a temperature of 0°–150° C., if appropriate in the presence of an organic or inorganic auxiliary base.

Depending on the choice of starting substances, the compounds according to the invention can exist in stereoisomeric forms, which either behave as mirror images (enantiomers) or do not behave as mirror images (diastereomers). The present invention relates to both the antipodes and the racemates and diastereomer mixtures. The racemates, like the diastereomers, can be separated into the pure stereoisomers in a known manner (compare E. L. Eliel, Stereochemistry of Carbon Compounds, McGraw Hill 1962).

Moreover, as a result of the double bond in the side chain, E/Z isomers of the compounds according to the invention are possible, and these can be prepared by known processes or converted into one another by known processes. Irradiation with UV rays, for example, may be mentioned as a known process.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation.

Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The carbonyl compounds of the general formula (II) which can be used as starting compounds are not yet known, but they can be prepared by methods analogous to known methods from imidazothiadiazoles of the formula (IX)

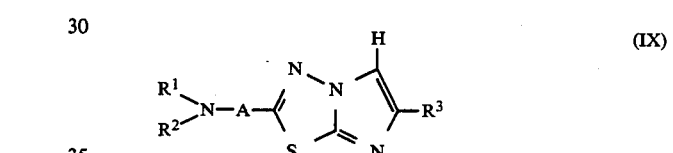

(IX)

in which A and $R^1$ to $R^3$ have the abovementioned meaning, by reacting these compounds with dimethylformamide in the presence of phosphorus oxychloride at temperatures from 20° C. to 170° C. (compare, for example, L. Pentimalli et al., Boll. Sci. Fac. Chim. Ind. Bologna 23, 181 (1965); C.A. 63, 17848 e (1965), D. Bower et al., J. Chem. Soc. 1955, 2834, A. Hetzheim et al., Che,. Ber. 103, 3333 (1970), H. Beyer et al., Z. Chem. 2, 152 (1962) and S. Kano, Yagukagu Zasski 92, 935 (1972)).

The alkenecarboxylic acids of the formula (VI) which can be used as starting compounds are also new. They can be prepared by known methods, by (a) reacting a carbonyl compound of the formula (II) with a phosphonate compound of the formula (X)

(X)

in which $R^5$, $R^{14}$ and $R^{15}$ have the abovementioned meaning and $R^{16}$ represents H, trialkyl or triarylsilyl or a radical with the same meaning as $R^{14}$, in the presence of a strong base in an inert organic solvent, to give the alkenecarboxylic acid derivative, and then hydrolysing this product with an acid or alkali to give the free carboxylic acid (compare W. S. Wadsworth et al., JACS 83, 1733 (1961)), or (b) reacting a carbonyl compound of the formula (II) in which $R^1$ to $R^3$ have the abovementioned meaning and $R^4$ is hydrogen (aldehydes), with a malonic acid of the formula $$R^5-CH(COOH)_2$$

in which $R^5$ has the abovementioned meaning,
or with Meldrum's acid in the presence of an inert organic solvent, if appropriate in the presence of a condensing agent (compare G. Jones, Org. Reactions, Volume 15, page 204 et seq.).

The imidazothiadiazole-alkenecarboxylic acid amides of the formula (VIII) which can be used as starting compounds can be obtained from corresponding hydroxyalkyl-imidazothiadiazole-alkenecarboxylic acid amides of the formula (XI)

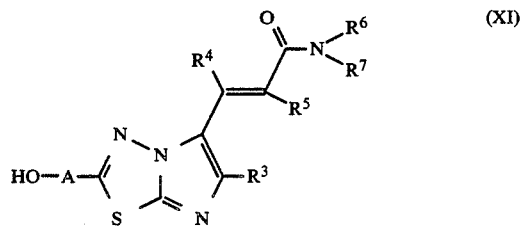

by reaction with a suitable halogenating agent (for example halides of 3-valent or 5-valent phosphorus, acid chlorides of sulphurous acid or acid chlorides of aliphatic carboxylic acids, preferably of oxalic acid) in the presence of dimethylformamide or other carboxylic acid amides in suitable organic solvents at temperatures from $-20°$ to $120°$ C. The imidazothiadiazole-alkenecarboxylic acid amides of the formula (XI) can be synthesised as described in DE-OS (German Published Specification) 3,043,158.

The phosphonate compounds of the formula (III) used in carrying out the preparation process according to the invention are known, or they can be prepared by known methods (compare I. Shahak et al. Isr. J. Chem. 7, 585 (1969)).

Examples which may be mentioned of strong bases for use in carrying out process variant (a) are: alkali metal hydrides, such as sodium hydride, potassium hydride and lithium hydride, and alkali metal alcoholates, such as sodium ethylate, potassium ethylate or potassium methylate, or alkali metal-alkyls, such as methyl-lithium or butyl-lithium.

The acetamide derivatives of the formula (V) used in carrying out process variant (b) are known, or they can be prepared by known methods (compare a) British Patent 715,896 (1954); and C.A. 49, 13290d (1955); and (b) German Patent Specification 1,142,859 (1960); and C.A. 59, 7377c (1963)).

Acid or basic catalysts are preferably used in this process variant (b), examples of these which may be mentioned being: basic amines, such as dialkylamines, piperidine or pyridine, or inorganic acids, in particular hydrochloric acid, or condensing agents, such as carboxylic acid anhydrides.

The alkenoic acids of the formula (VI) used according to process variant (c) have not yet been disclosed, but can be prepared in a manner which is known per se by the abovementioned processes. The activation of the free carboxyl group, which is advantageous for the reaction with amines, is preferably carried out via the corresponding acid halide, in particular via the corresponding acid chloride, using halide-forming agents, such as, for example, thionyl chloride, phosphorus trichloride and phosphorus pentachloride.

The customary inert organic solvents can be used as diluents in all the processes according to the invention. These solvents include, preferably, ethers, such as diethyl ether, glycol ethers, such as glycol dimethyl ether, dioxane and tetrahydrofuran, or alcohols, such as methanol, ethanol, propanol, butanol and benzyl alcohol, or sulphoxides, such as dimethylsulphoxide, bases, such as pyridine, quinoline and piccoline, or hydrocarbons, such as benzene, toluene and xylene, and dimethylformamide.

Bases which are preferably used for the hydrolysis of the corresponding esters in the preparation of the alkenoic acids of the formula (VI) are: alkali metal hydroxides, such as sodium hydroxide and potassium hydroxide, or alkaline earth metal hydroxides, such as barium hydroxide or calcium hydroxide.

Condensing agents which are preferably used in the preparation via the aldehydes of the formula (II) with $R^4=H$ with malonic acids of the formula $R^5-CH(COOH)_2$ are: pyridine, substituted pyridine derivatives, such as dialkylaminopyridines, quinoline, isoquinoline, dialkylamines, such as dimethylamine and dibutylamine, pyrrolidine, piperidine and similar nitrogen-containing organic bases.

The invention also relates to the carbonyl compounds of the formula (II) which can be used as intermediates and the alkenecarboxylic acids of the tormula (VI) and the processes for their prepara- tion.

The compounds according to the invention are distinguished, surprisingly, by powerful biological actions. In particular, they have pronounced diuretic and saluretic actions and can therefore be used as diuretics, saluretics and antihypertensive agents. In animal experiments on mice, rats and dogs, it is found that, on oral administration, the compounds according to the invention already have a pronounced diuretic and saluretic action, at the same time coupled with good tolerance, at dosages below 10 mg/kg. These advantageous properties were not to be expected from the knowledge of the prior art.

The surprising and advantageous actions of the compounds according to the invention can be determined by the following test methods:

(A) Antihypertensive action in rats

The effect on blood pressure is determined on Goldblatt hypertensive rats in accordance with the method of H. Breuninger: Methoden zur unblutigen Messung des Blutdruckes an Kleintieren (Methods of non-operative measurement of the blood pressure on small animals), Arzneimittelforsch. 6, 222–225 (1965).

(B) Diuretic action on rats

Fasting male rats weighing 150 to 250 g (SPF, Wistar, each n=4 pairs) are treated with 10 ml/kg of tylose suspension (0.5%) perorally, as controls, or with 100 mg/kg of test substance perorally in 10 ml/kg of tylose suspension perorally by means of a stomach tube. The animals are put into metabolism cages and the excretion of the urine and electrolytes is determined over 6 hours ($Na^+$ and $K^+$ determination: IL flame photometer).

(C) Diuretic action on dogs

The urinary bladder of fasting, conscious female beagle dogs is catheterised and the excretion of urine and electrolytes is determined over 180 minutes (divided into fractions, each of 30 minutes).

The animals receive a continuous intravenous infusion of an electrolyte solution during this period, and the test substance orally in 1 ml/kg of tylose suspension (0.5%) at the start of the experiment.

The urine is analysed for $Na^+$, $K^+$, chlorine, bicarbonate and pH.

(D) Diuretic action on mice

Fasting male SPF mice weighing 20 to 25 g ($n = 6 \times 3$ animals/cage) receive 100 ml/kg of tylose suspension (0.5%), as controls, or 100 mg/kg of test substance in tylose suspension orally.

The excretion of urine, $Na^+$ and $K^+$, and uric acid is determined in metabolism cages over 2 and 4 hours.

(E) Phenol red retention test on rats

To demonstrate uricosuric activity, the influence of compounds according to the invention on the blood phenol red level is determined on conscious, fasting male rats (SPF-Wistar, weight: 180 to 250 g). In accordance with the method of E. Kreppel (Med. exp. 1 (1959), 285–289), groups of 8 animals receive 75 mg/kg of phenol red in 5 ml/kg of saline solution intraperitoneally, after either 10 mg/kg of tylose suspension (0.5%), as controls, or 100 mg/kg of test substance in tylose suspension had been administered 30 minutes beforehand. Plasma is obtained by puncture of the retroorbital venous plexus 30, 60 and 120 minutes after administration of phenol red, or 60, 90 and 150 minutes after administration of the substance, NaOH is added and the extinction is determined at 546 nm in a photometer (Eppendorf).

Potential uricosuric activity exists if the extinction values are significantly higher than in the control group.

The new compounds according to the invention are substances which can be used as medicaments. When administered orally or parenterally, they cause an increase in the excretion of water and salts and can therefore be used for the treatment of oedematous and hypertonic conditions and for flooding out toxic substances.

The compounds can also be used in cases of acute renal failure. In particular, they also have an advantageous uricosuric action.

The new compounds can be converted in a known manner into the customary formulations, such as tablets, capsules, dragees, pills, granules, syrups, emulsions, suspensions and solutions, using inert, non-toxic, pharmaceutically suitable excipients or solvents. The therapeutically active compound should in each case be present in these formulations in a concentration of about 0.5 to 90% by weight of the total mixture, that is to say in amounts which are sufficient to achieve the dosage range given below.

The formulations are prepared, for example, by extending the active compounds with solvents and/or excipients, if necessary using emulsifying agents and/or dispersing agents, and, for example, in the case of the use of water as the diluent, organic solvents may also be used, if appropriate, as auxiliary solvents.

Administration is effected in the customary manner, preferably orally or parenterally.

In the case of parenteral administration, solutions of the active compounds can be employed, using suitable liquid excipients. The fact that the compounds according to the invention are capable of forming readily water-soluble salts has proved to be particularly advantageous in the case of parenteral administration. Salts of this type can also have an increased importance for oral administration of the compounds according to the invention in that they accelerate or delay the absorption as required.

In general, it has proved advantageous, on parenteral administration, to administer amounts of about 0.05 to 100 mg/kg of body weight, preferably about 0.1 to 10 mg/kg of body weight, daily to achieve effective results. In the case of oral administration, the dosage is about 0.1 to 500 mg/kg of body weight, preferably 0.5 to 100 mg/kg of body weight, daily.

Nevertheless, it may at times be necessary to deviate from the amounts mentioned, and in particular to do so as a function of the body weight of the experimental animals or of the nature of the administration route, but also because of the animal species and its individual behaviour towards the medicament or the nature of its formulation and the time or interval at which administration takes place. Thus, it can in some cases be sufficient to manage with less than the abovementioned minimum amount, whilst in other cases the upper limit mentioned must be exceeded. Where relatively large amounts are administered, it may be advisable to divide these into several individual doses over the day.

Example 1 which follows illustrates the preparation of the imidazothiadiazoles of the (IX) used according to the invention as starting substances.

Example 2 illustrates the preparation of the carbonyl compounds of the formula (II) used according to the invention.

The examples which then follow illustrate the preparation of the imidazolealkenoic acid amides of the formula (I) according to the invention (Table 1).

EXAMPLE 1

Preparation of imidazothiadiazoles of the formula (IX)

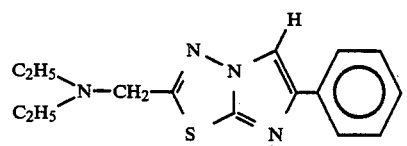

2-Diethylaminomethyl-6-phenyl-imidazo[2,1-b]-1,3,4-thiadiazole 18.6 g (0.1 mol) of 2-amino-5-diethylaminomethyl-1,3,4-thiadiazole and 19.9 g of ω-bromo-acetophenone in 70 mL of dimethylformamide are warmed at 150° C. for 3 hours. 150 ml of water are added to the cooled reaction mixture and the mixture is neutralised with 20% strength sodium hydroxide solution. The precipitate is filtered off with suction. After recrystallisation from acetonitrile, 11.5 g (40.2%) of melting point 138° C. remain.

EXAMPLE 2

Preparation of the carbonyl compounds of the general formula (II)

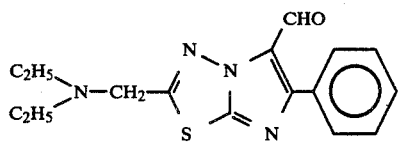

2-Diethylaminomethyl-6-phenyl-imidazo[2,1-b]-1,3,4-thiadiazol-5-carbaldehyde 2.3 ml (0.025 mol) of phosphorus oxychloride are added dropwise to 20 ml of dimethylformamide at 0°–5° C. 5.7 g (0.02 mol) of 2-diethylaminomethyl-6-phenyl-imidazo-[2,1-b]-1,3,4-thiadiazole are then added and the mixture is warmed at 100° C. for 2 hours. After cooling, 50 ml of water are added and the mixture is neutralised with 20% strength sodium hydroxide solution and extracted with ether.

After concentration, the crude product is recrystallised from ether/petroleum ether.

Yield: 3.0 g (48%), melting point: 60° C.

Examples for the preparation of aminoalkyl-imidazothiadiazole-alkenecarboxamides of the formula (I)

EXAMPLE 3

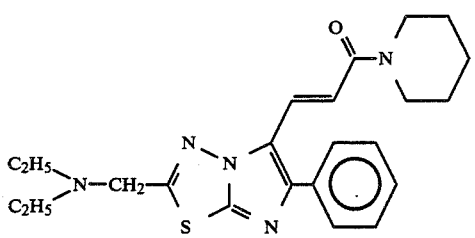

β-(2-Diethylaminomethyl-6-phenyl-imidazo-[2,1-b]-1,3,4-thiadiazol-5-yl)-E-propenoyl piperidide 2.9 g (0.011 mol) of diethylphosphonoacetic acid piperidide are added to 0.33 g of 80% sodium hydride (0.011 mol; de-oiled with petroleum ether) in 100 ml of toluene (anhydrous) and the mixrture is warmed at 60° C. until the evolution of hydrogen has ended. 2.86 g of 2-diethylaminomethyl-6-phenyl-imidazo-[2,1-b]-1,3,4-thiadiazol-5-carbaldehyde are added at room temperature and the mixture is stirred at 50° C. for one hour. After cooling, the mixture is extracted by shaking with two portions of 10% strength sodium carbonate solution and the extracts are dried over sodium sulphate and concentrated.

The crude product is recrystallised from isopropanol.
Yield: 2.75 g (65%), melting point: 176° C.

EXAMPLE 4

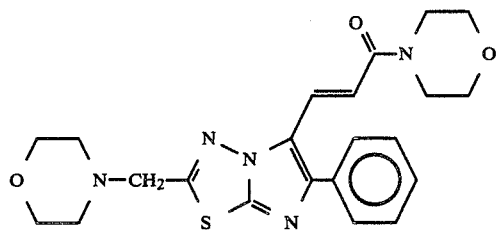

β-(2-Morpholinomethyl-6-phenyl-imidazo-[2,1-b]-1,3,4-thiadiazol-5-yl)-E-propenoyl morpholide 1.3 g of oxalyl chloride are added dropwise to a solution of 1 g of dimethylformamide in 50 ml of methylene chloride at 5–10° C. After 30 minutes, 3.7 g of β-(2-hydroxymethyl-6phenyl-imidazo-[2,1-b]-1,3,4-thiadiazol-5-yl)-E-propenoyl morpholide are added and the mixture is warmed under reflux for 30 minutes. 2 g of morpholine are then added and the mixture is warmed under reflux for 1 hour. After the mixture has been extracted by shaking with water and dried over sodium sulphate, it is concentrated and the residue is recrystallised from chloroform/ether.

Yield: 2.4 g (55%), melting point: 207-9° C.

The compounds according to Table 1 are synthesised analogously.

TABLE 1

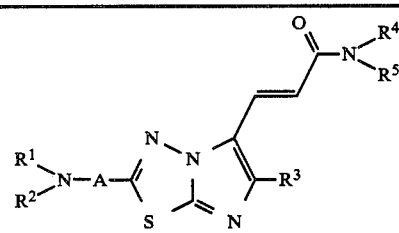

| Example No. | A | $R^1$ | $R^2$ | $R^3$ | $R^4$ | $R^5$ | Yield | Melting point |
|---|---|---|---|---|---|---|---|---|
| 5 | —CH$_2$— | C$_2$H$_5$ | C$_2$H$_5$ | C$_6$H$_5$ | C$_2$H$_5$ | C$_2$H$_5$ | 73% | 104° C. |
| 6 | —CH$_2$— | C$_2$H$_5$ | C$_2$H$_5$ | C$_6$H$_5$ | 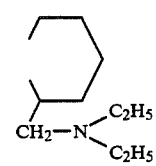 | | 30% | 124–5° C. |

TABLE 1-continued

[Structure: pyrazole core with R¹R²N-A-C(=S)- group on one nitrogen and -CH=CH-C(=O)-NR⁴R⁵ chain with R³ substituent]

| Example No. | A | R¹ | R² | R³ | R⁴ | R⁵ | Yield | Melting point |
|---|---|---|---|---|---|---|---|---|
| 7 | —CH₂— | C₂H₅ | C₂H₅ | C₆H₅ | \multicolumn{2}{c|}{4-methylcyclohexyl (NR⁴R⁵ = 4-methylpiperidino)} | 35% | 138–40° C. |
| 8 | —CH₂— | C₂H₅ | C₂H₅ | C₆H₅ | \multicolumn{2}{c|}{piperidino} | 73% | 214° C. |
| 9 | —CH₂— | C₂H₅ | C₂H₅ | C₆H₅ | \multicolumn{2}{c|}{morpholino} | 61% | 181° C. |
| 10 | —CH₂— | C₂H₅ | C₂H₅ | C₆H₅ | \multicolumn{2}{c|}{4-ethylpiperidino} | 50% | 106–7° C. |
| 11 | —CH₂— | C₆H₅ | CH₃ | C₆H₅ | \multicolumn{2}{c|}{morpholino} | 41% | 155° C. |
| 12 | —CH₂— | \multicolumn{2}{c|}{2-ethylpiperidino} | C₆H₅ | \multicolumn{2}{c|}{morpholino} | 28% | 160° C. |
| 13 | —CH₂— | \multicolumn{2}{c|}{morpholino} | C₆H₅ | \multicolumn{2}{c|}{4-ethylpiperidino} | 56% | 194° C. |
| 14 | —CH₂— | \multicolumn{2}{c|}{2-ethylpiperidino} | C₆H₅ | \multicolumn{2}{c|}{4-ethylpiperidino} | 40% | 117–9° C. |
| 15 | —CH₂— | \multicolumn{2}{c|}{2-ethylpiperidino} | C₆H₅ | C₂H₅ | C₂H₅ | 38% | 129–30° C. |

TABLE 1-continued

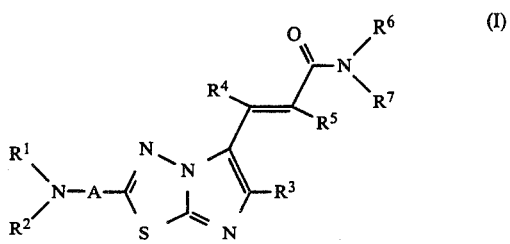

| Example No. | A | R¹ | R² | R³ | R⁴ | R⁵ | Yield | Melting point |
|---|---|---|---|---|---|---|---|---|
| 16 | —$CH_2$— | \_N_O_/ (morpholine) | | $C_6H_5$ | $C_2H_5$ | $C_2H_5$ | 70% | 173–4° C. |
| 17 | —$CH_2$— | $C_6H_5$ | $CH_3$ | $C_6H_5$ | $C_2H_5$ | $C_2H_5$ | 23% | 125° C. |
| 18 Hydrochloride | —$CH_2$— | $C_2H_5$ | $C_2H_5$ | $C_6H_5$ | (cyclohexyl) | | 80% | 210° C. |

What is claimed is:

1. A compound of the formula (I)

$$\text{(I)}$$

in which

R¹ denotes hydrogen, aryl or an aliphatic hydrocarbon radical which is optionally interrupted by O, S, N, N-alkyl or NH and is optionally substituted by hydroxyl, alkoxy, alkyl, trifluoromethyl, halogen, alkoxycarbonyl or dialkylamino, the two alkyl radicals optionally forming, together with the N atom, a 5-membered to 7-membered ring which is optionally interrupted by a heteroatom from the group comprising O, S, NH and N-aklyl, and these abovementioned alkyl and phenyl radicals in turn optionally being substituted by halogen, trifluoromethyl, alkyl, alkoxy, alkylmercapto or $SO_2$-aklyl, R² has the meaning given for R¹, it being possible for R² and R¹ to be identical or different, or R² together with R¹ forms, with the nitrogen atom, a 5-membered to 7-membered saturated or unsaturated ring which optionally contains 1 or 2 further hetero-atoms from the group comprising oxygen, sulphur and nitrogen, the nitrogen optionally being substituted by hydrogen or alkyl, and it being possible for this 5-membered to 7-membered ring to be substituted by 1 to 4 identical or different substituents from the group comprising alkyl, halogen, aryl, aralkyl, alkoxycarbonyl, hydroxyalkyl, alkoxyalkyl and trifluoromethyl, A represents a chain 1–4 carbon atoms which is optionally interrupted by a hetero-atom from the group comprising oxygen, sulphur and nitrogen and can be saturated or unsaturated or part of a 4-membered to 7-membered ring, and in which each nitrogen and carbon atom can be substituted by radicals R¹, which can be identical or different, R³ represents a phenyl, naphthyl, furyl, thienyl, pyrimidyl, pyrazinyl, quinolyl, isoquinolyl or pyridyl radical which is optionally substituted by 1 to 3 identical or different substituents from the group comprising halogen, nitro, trifluoromethyl, alkyl, alkoxy, dialkylamino and $SO_n$-alkyl (n=0, 1 or 2), the alkyl and alkoxy radicals mentioned in each case containing 1–4 carbon atoms, R⁴ represents hydrogen, trifluoromethyl or alkyl, R⁵ represents hydrogen, alkyl, cyano, halogen or $CXR^8$, wherein X denotes O or S and R⁸ has the abovementioned meaning of R¹, and R⁶ and R⁷ each have the meaning given for R¹ and are identical to or different from R¹, or together with the nitrogen atom form a 5-membered to 7-membered saturated or unsaturated ring which optionally contains 1 or 2 further hetero-atoms from the group comprising oxygen, sulphur and nitrogen, the nitrogen optionally being substituted by hydrogen, alkyl with 1 to 4 carbon atoms, phenyl or benzyl, and its stereoisomeric forms of the various enantiomers, diastereomers and E/Z isomers and its pharmaceutically acceptable acid addition salts.

2. A compound of the formula (I) according to claim 1, in which,

R¹ denotes hydrogen or a straight-chain, branched or cyclic, saturated aliphatic hydrocarbon radical which is optionally interrupted by O, S, N, N-alkyl or NH and is optionally substituted by hydroxyl, alkoxy, alkyl, trifluoromethyl, halogen, alkoxycarbonyl or dialkylamino, R² has the meaning given for R¹, it being possible for R² and R¹ to be identical or different, or R² together with R¹ forms, with the nitrogen atom, a 5-membered to 7-membered saturated or unsaturated ring which optionally contains 1 or 2 further hetero-atoms from the group comprising oxygen, sulphur and nitrogen, the nitrogen optionally being substituted by hydrogen or alkyl, and it being possible for this 5-membered to 7-membered ring to be substituted by 1 to 4 identical or different substituents from the group comprising alkyl, halogen, aryl, aralkyl, alkoxycarbonyl, hydroxyalkyl, alkoxyalkyl and trifluoromethyl, A represents a chain of 1–4 carbon atoms which is optionally interrupted by oxygen or nitrogen and can be saturated or unsaturated or part of a 4-membered to 7-membered ring, and in which each nitrogen or carbon atom can be substituted by radicals $R^1$, which can be identical or different, $R^3$ represents a phenyl, furyl, naphthyl, thienyl, pyrimidyl, pyrazinyl, quinolyl, isoquinolyl or pyridyl radical which is optionally substituted by one or two identical or different substituents from the group comprising halogen, nitro, trifluoromethyl, alkyl, alkoxy, dialkylamino and S-alkyl, the alkyl and alkoxy radicals mentioned in each case containing 1 to 4 carbon atoms, $R^4$ and $R^5$ are identical or different and represent hydrogen or alkyl with 1 to 4 carbon atoms and $R^6$ and $R^7$ have the meaning given for $R^1$ and are identical to or different from $R^1$, or together with the nitrogen atom form a 5-membered to 7-membered ring which is optionally interrupted by an oxygen or nitrogen atom, the nitrogen optionally being substituted by hydrogen, alkyl with 1–4 carbon atoms or benzyl, and its stereoisomeric forms of the various enantiomers, diastereomers and Z/E isomers and its pharmaceutically acceptable acid addition salts.

3. A compound of claim 1 wherein $R^1$ is $C_1$–$C_4$-alkyl or phenyl; $R^2$ is $C_1$–$C_4$-alkyl; $R^1$+$R^2$ taken together with the nitrogen atom which joins them is piperidino which is unsubstituted or substituted on a ring carbon atom by $C_1$–$C_4$-alkyl; or morpholino; $R^3$ is phenyl; $R^4$ is $C_1$–$C_4$-alkyl; $R^5$ is $C_1$–$C_4$-alkyl; and $R^4$ and $R^5$, taken together with the nitrogen atom which joins them is piperidino which is unsubstituted or substituted on a ring-carbon-atom by (a) mono- or di-$C_1$–$C_4$-alkyl amino-$C_1$–$C_4$-alkyl or (b) $C_1$–$C_4$-alkyl; or morpholino.

4. A compound of claim 3 wherein $R^1$ and $R^2$ are ethyl and $R^4$ and $R^5$ are ethyl.

5. A compound of claim 3 wherein $R^1$ and $R^2$ are ethyl and $R^4$ and $R^5$, taken together with the nitrogen atom which joins them are morpholino, piperidino or piperidino substituted by $C_1$–$C_4$-alkyl.

6. A compound of formula (I) according to claim 1 which is β-(2-diethylaminomethyl-6-phenyl-imidazo[2,1-b]-1,3,4-thiadiazol-5-yl)-E-propenoyl piperidide or a stereoisomer or acid addition salt thereof.

7. A compound of formula (I) according to claim 1 which is β-(2-diethylaminomethyl-6-phenyl-imidazo[2,1-b]-1,3,4-thiazol-5-yl)-E-propenoyl diethylaminide or a stereoisomer or acid addition salt thereof.

8. A compound of formula (I) according to claim 1 which is β-(2-diethylaminomethyl-6-phenyl-imidazo[2,1-b]-1,3,4-thiazol-5-yl)-E-propenoyl 2-methyl piperidide or a stereoisomer or acid addition salt thereof.

9. A compound of formula (I) according to claim 1 which is β-(2-diethylaminomethyl-6-phenyl-imidazo[2,1-b]-1,3,4-thiazol-5-yl)-E-propenoyl 2-ethyl piperidide or a stereoisomer or acid addition salt thereof.

10. A compound of formula (I) according to claim 1 which is β-(2-morpholinomethyl-6-phenyl-imidazo[2,1-b]1,3,4-thiazol-5-yl)-E-propenyl piperidide hydrochloride.

11. A pharmaceutical composition containing, as an active ingredient, an anti-hypertensive-, diuretic- or uricosuric-effective amount of a compound according to claim 1 in admixture with an inert pharmaceutical carrier.

12. A pharmaceutical composition containing, as an active ingredient, an anti-hypertensive-, diuretic- or uricosuric-effective amount of a compound of claim 1 in the form of a sterile or physiologically isotonic aqueous solution.

13. A composition according to claim 11 containing from 0.5 to 90% by weight of the said active ingredient.

14. A medicament in dosage unit form comprising an anti-hypertensive-, diuretic- or uricosuric-effective amount of a compound according to claim 1 and an inert pharmaceutical carrier.

15. A medicament of claim 14 in the form of tablets, pills, dragees, capsules, ampules or suppositories.

16. A method of effecting hypotension, diuresis or uricosuria in warm-blooded animals which comprises administering to the animals an effective amount of an active compound according to claim 1, either alone or in admixture with an inert pharmaceutical carrier or in the form of a medicament.

17. A method according to claim 16 in which the active compound is administered in an amount of 0.05 to 100 mg/kg body weight parenterally or in an amount about 0.1 to 500 mg/kg body weight orally.

18. A method according to claim 16 in which the active compound is administered orally 19. A method according to claim 16 in which the active compound is administered parenterally.

20. Alkenecarboxylic acids of the formula (VI)

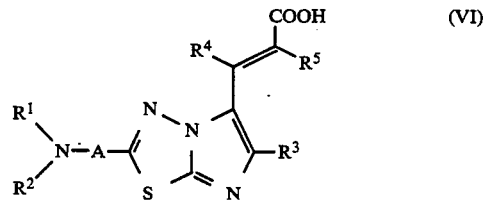

in which $R^1$ denotes hydrogen, aryl or an aliphatic hydrocarbon radical which is optionally interrupted by O, S, N, N-alkyl, NH, N-aryl or N-aralkyl and is optionally substituted by hydroxyl, alkoxy, alkyl, trifluoromethyl, halogen, phenyl, alkoxycarbonyl or dialkylamino, it being possible for the two alkyl radicals optionally to form, together with the N atom, a 5-membered to 7-membered ring, which is optionally interrupted by a hetero-atom from the group comprising O, S, NH and N-alkyl, and these abovementioned alkyl and phenyl radicals in turn optionally being substituted by halogen, trifluoromethyl, alkyl, aryl, aralkyl, alkoxy, alkylmercapto or $SO_2$-alkyl, $R^2$ has the meaning given for $R^1$, it being possible for $R^2$ and $R^1$ to be identical or different, or $R^2$ together with $R^1$ forms, with the nitrogen atom, a 3-membered to 8-membered saturated or unsaturated ring which optionally contains 1 or 2 other hetero-atoms from the group comprising oxygen, sulphur and nitrogen, the nitrogen optionally being substituted by hydrogen, alkyl, aryl or aralkyl, and it being possible for this 3-membered to 8-membered ring to be substituted by 1 to 4 identical or different substituents from the group comprising alkyl, halogen, aryl, aralkyl, alkoxycarbonyl, hydroxyalkyl, alkoxyalkyl and trifluoromethyl, or it being possible for this ring to be fused with an aromatic ring, A represents a chain of 1–4 carbon atoms which is optionally interrupted by 1 or 2 hetero-atoms from the group comprising oxygen, sulphur and nitrogen and can be saturated or unsaturated or part of a 3-membered to 8-membered ring, and in which each nitrogen and carbon atom can be substituted by radicals $R^1$, which can be identical or different, $R^3$ has the meaning given for $R^1$ and is identical to or different from $R^1$, or represents furyl, phenyl, thienyl, pyrimidyl, pyrazinyl, quinolinyl, isoquinolinyl or pyridyl, the rings optionally being substituted by 1, 2 or 3 identical or different substituents from the group comprising alkyl, aryl, alkoxy, halogen, nitro, trifluoromethyl, $SO_n$-alkyl (n=0, 1 or 2) or $NR^9R^{10}$, wherein
$R^9$ and $R^{10}$ have the abovementioned means of $R^1$ and $R^2$, $R^4$ represents hydrogen, trifluoromethyl or alkyl and $R^5$ represents hydrogen, alkyl, cyano, halogen, nitro, $SO_n$-alkyl (N=0, 1 or 2) or $CXR^8$, wherein
X denotes O or S and
$R^8$ has the abovementioned meaning of $R^1$.

* * * * *

UNITED STATES PATENT AND TRADEMARK OFFICE
CERTIFICATE OF CORRECTION

PATENT NO. : 4,588,723

DATED : May 13, 1986

INVENTOR(S) : Axel Ingendoh, et al.

It is certified that error appears in the above-identified patent and that said Letters Patent is hereby corrected as shown below:

| | |
|---|---|
| Col. 3, line 13 | Delete "interrupt" and substitute --interrupted by-- |
| Col. 8, line 32 | Delete "prepara- tion" and substitute --preparation-- |
| Col. 9, line 43 | Delete "sub- stances" and substitute --substances-- |
| Col. 10, line 61 | Delete "mL" and substitute --ml-- |
| Col. 12, line 32 | After "6" insert -- - -- |
| Col. 17, line 67 | After "b]" insert -- - -- |
| Col. 19, line 14 | Delete "phenyl" |
| Col. 20, line 7 | Delete "means" and substitute --meanings-- |

Signed and Sealed this

Sixteenth Day of September 1986

[SEAL]

Attest:

DONALD J. QUIGG

Attesting Officer    Commissioner of Patents and Trademarks